(12) United States Patent
Stein et al.

(10) Patent No.: US 6,677,130 B1
(45) Date of Patent: *Jan. 13, 2004

(54) MITOGEN-ACTIVATED PROTEIN KINASE P38-2 AND METHODS OF USE THEREFOR

(75) Inventors: Bernd Stein, San Diego, CA (US); Maria X. H. Yang, San Diego, CA (US); David B. Young, San Diego, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 09/724,768

(22) Filed: Nov. 28, 2000

Related U.S. Application Data

(60) Continuation of application No. 09/295,029, filed on Apr. 20, 1999, now Pat. No. 6,444,455, which is a division of application No. 08/651,940, filed on May 20, 1996, now Pat. No. 5,948,885.

(51) Int. Cl.$^7$ .............................. A01N 1/00; C12N 9/00; C12N 9/10; C12N 9/12

(52) U.S. Cl. .............................. 435/15; 435/4; 435/183; 435/193; 435/194

(58) Field of Search ............................ 435/4, 183, 193, 435/194, 15

(56) References Cited

U.S. PATENT DOCUMENTS 6,074,862 A   6/2000 Stein et al. ................. 435/194

FOREIGN PATENT DOCUMENTS

| WO | WO 95/07922 | | 3/1995 |
|---|---|---|---|
| WO | WO 95/07922 A | * | 3/1995 |
| WO | WO 95/21923 | | 8/1995 |
| WO | WO 96/36642 | | 11/1996 |

OTHER PUBLICATIONS

Adams et al. GenBank Acc No. AAR71677, Oct. 22, 1995.*
Han et al. GenBank Acc. No. S53536, Jul. 15, 1995.*
Han et al. BBA, 1995, vol. 1265:224–227.*
Rouse et al. GenBank Accession No. A54805, Oct. 28, 1994.*
Rouse et al. Cell, 1994, vol. 78:1027–1037.*
Cano and Mahadevan. 1995. Parallel signal processing among mammalian MAPKs. Trends Biochem Sci. 20(3):117–22.
Cobb and Goldsmith. 1995. How MAP kinases are regulated. Biol Chem. 270(25):14843–6.
Cobb et al. 1991. "Extracellular Regulated Kinases: ERKs in Progress." Cell Regulation 2:965–977.
Davis R. 1994. "MAPKs: New JNK expands the group" Trends Biochem Sci. 19:470–473.

Derijard et al. 1995. Independent human MAP–kinase signal transduction pathways defined by MEK and MKK isoforms. Science. 267(5198):682–5.
Derijard et al. 1994. JNK1: a protein kinase stimulated by UV light and Ha–Ras that binds and phosphorylates the c–Jun activation domain. Cell. 76(6):1025–37.
Gupta et al. 1995. Transcription factor ATF2 regulation by the JNK signal transduction pathway. Science. 267(5196):389–93.
Han et al. 1994. A MAP kinase targeted by endotoxin and hyperosmolarity in mammalian cells. Science. 265(5173):808–11.
Han et al. 1995. Molecular cloning of human p38 MAP kinase. Biochim Biophys Acta. 1265(2–3):224–7.
Herskowitz I. 1995. MAP kinase pathways in yeast: for mating and more. Cell. 80(2):187–97.
Hunter and Karin. 1992. The regulation of transcription by phosphorylation. Cell. 70(3):375–87.
Hunter T. 1995. Protein kinases and phosphatases: the yin and yang of protein phosphorylation and signaling. Cell. 80(2):225–36.
Jiang et al. 1996. Characterization of the structure and function of a new mitogen–activated protein kinase (p38beta). J Biol Chem. 271(30):17920–6.
Karin and Smeal. 1992. Control of transcription factors by signal transduction pathways: the beginning of the end. Trends Biochem Sci. Oct. 1992;17(10):418–22.
Kumar et al. 1997. Novel homologues of CSBP/p38 MAP kinase: activation, substrate specificity and sensitivity to inhibition by pyridinyl imidazoles. Biochem Biophys Res Commun. 235(3):533–8.
Lee et al. 1994. A protein kinase involved in the regulation of inflammAtory cytokine biosynthesis. Nature. 372(6508):739–46.
Li et al. 1996. The primary structure of p38 gamma: a new member of p38 group of MAP kinases. Biochem Biophys Res Commun. 228(2):334–40.
Lin et al. 1995. Identification of a dual specificity kinase that activates the Jun kinases and p38–Mpk2. Science. 268(5208):286–90.
Minden et al. 1994. Differential activation of ERK and JNK mitogen–activated protein kinases by Raf-1 and MEKK. Science. 266(5191):1719–23.

(List continued on next page.)

Primary Examiner—Rebecca E. Prouty
Assistant Examiner—Manjunath N. Rao
(74) Attorney, Agent, or Firm—Pennie & Edmonds LLP

(57) ABSTRACT

Compositions and methods are provided for the treatment of diseases associated with mitogen activated protein kinase cascades. In particular, the mitogen-activated protein kinase p38-2, and polypeptide variants thereof that stimulate phosphorylation and activation of substrates such as ATF2, are provided. The polypeptides may be used, for example, to identify antibodies and other agents that inhibit or activate signal transduction via the p38-2 kinase cascade. Such polypeptides and agents may also be used for the treatment of diseases associated with mitogen-activated protein kinase cascades.

5 Claims, 6 Drawing Sheets

OTHER PUBLICATIONS

Moriguchi et al. 1995. Evidence for multiple activators for stress–activated protein kinase/c–Jun amino–terminal kinases. Existence of novel activators. J Biol Chem. 270(22):12969–72.

Nahas et al. 1996.Tyrosine phosphorylation and activation of a new mitogen–activated protein (MAP)–kinase cascade in human neutrophils stimulated with various agonists. Biochem J. 318 ( Pt 1):247–53.

Pang et al. 1995. Inhibition of MAP kinase kinase blocks the differentiation of PC–12 cells induced by nerve growth factor. J Biol Chem. 270(23):13585–8.

Rouse et al. 1994. A novel kinase cascade triggered by stress and heat shock that stimulates MAPKAP kinase–2 and phosphorylation of the small heat shock proteins. Cell. 78(6):1027–37.

Sanchez et al. 1994. Role of SAPK/ERK kinase–1 in the stress–activated pathway regulating transcription factor c–Jun. Nature. 372(6508):794–8.

Seger and Krebs. 1995. The MAPK signaling cascade. FASEB J. 9(9):726–35.

Yan et al. 1994. Activation of stress–activated protein kinase by MEKK1 phosphorylation of its activator SEK1. Nature. 372(6508):798–800.

Yashar et al. 1993. Novel members of the mitogen–activated protein kinase activator family in *Xenopus laevis*. Mol Cell Biol. 13(9):5738–48.

Zhou et al. 1995. Novel members of the mitogen–activated protein kinase activator family in *Xenopus laevis*. Mol Cell Biol. Sep. 1993;13(9):5738–48.

Ben–Levy et al. 1995. Identification of novel phosphorylation sites required for activation of MAPKAP kinase–2. EMBO J. 14(23):5920–30.

Bradford MM. 1976. A rapid and sensitive method for the quantitation of microgram quantities of protein utilizing the principle of protein–dye binding. Anal Biochem. 72:248–54.

Fraley et al. 1981. Trends Biochem Sci. 6:77–80.

Kawai and Nishizawa. 1984. New procedure for DNA transfection with polycation and dimethyl sulfoxide. Mol Cell Biol. 4(6):1172–4.

Kohler G, and Milstein C. 1976. Derivation of specific antibody–producing tissue culture and tumor lines by cell fusion. Eur J Immunol. 6(7):511–9.

Mannino RJ, and Gould–Fogerite S. 1988. Liposome mediated gene transfer. Biotechniques. 6(7):682–90.

McLaughlin et al. 1996.Identification of mitogen–activated protein (MAP) kinase–activated protein kinase–3, a novel substrate of CSBP p38 MAP kinase. J Biol Chem. 271(14):8488–92.

McNalley et al. 1988. Optimizing electroporation parameters for a variety of human hematopoietic cell lines. Biotechniques. 6(9):882–6.

Ulmer et al. 1993. Heterologous protection against influenza by injection of DNA encoding a viral protein. Science. 259(5102):1745–9.

Yamaguchi et al. 1995. Identification of a member of the MAPKKK family as a potential mediator of TGF–beta signal transduction. Science. 270(5244):2008–11.

* cited by examiner p38-2 p38-2:  1 MSGPRAGFYRQELNKTVWEVPQRLQGLRPVGSGAYGSVCSAYDARLRQKVAVKKLSRPFQ 60

: 61 SLIHARRTYRELRLLKHLKHENVIGLLDVFTPATSLEDFSEVYLVTTLMGADLNNIVKCQ 120

: 121 ALSDEHVQFLVYQLLRGLKYIHSAGIIHRDLKPSNVAVNEDCELRILDFGLARQADEEMT 180

: 181 GYVATRWYRAPEIMLNWMHYNQTVDIWSVGCIMAELLQGKALFPGSDYIDQLKRIMEVVG 240

: 241 TPSPEVLAKISSEHARTYIQSLPPMPQKDLSSIFRGANPLAIDLLGRMLVLDSDQRVSAA 300

: 301 EALAHAYFSQYHDPEDEPEAEPYDEGVEAKERTLEEWKELTYQEVLSFKPPEPPKPPGSL 360

: 361 EIEQ* 364

ALTERNATIVE SPLICED FORMS p38-2:  1 MSGPRAGFYRQELNKTVWEVPQRLQGLRPVGSGAYGSVCSAYDARLRQKVAVKKLSRPFQ 60

: 61 SLIHARRTYRELRLLKHLKHENVIGLLDVFTPATSIEDFSEV* 120 p38-2:  1 MSGPRAGFYRQELNKTVWEVPQRLQGLRPVGSGAYGSVCSAYDARLRQKVAVKKLSRPFQ 60

: 61 SLIHARRTYRELRLLKHLKHENVIGLLDVFTPATSIEDFSEVYLVTTLMGADLNNIVKCQ 120

: 121 ALSDEHVQFLVYQLLRGLKYIHSAGIIHRVGATAG* 155

*Fig. 1*

| | |
|---|---|
| ggac atg tcg ggc cct cgc gcc ggc ttc tac cgg cag gag ctg aac aag<br>     M   S   G   P   R   A   G   F   Y   R   Q   E   L   N   K | 49 |
| acc gtg tgg gag gtg ccc cac ccc ctc cag ggg ctg cgc ccg gtc ggc<br> T   V   W   E   V   P   H   P   L   Q   G   L   R   P   V   G | 97 |
| tcc ggc gcc tac ggc tcc gtc tgt tcg gcc tac gac gcc cgg ctg cgc<br> S   G   A   Y   G   S   V   C   S   A   Y   D   A   R   L   R | 145 |
| cag aag gtg gcg gtg aag aag ctg tcg cgc ccc ttc cag tcg ctg atc<br> Q   K   V   A   V   K   K   L   S   R   P   F   Q   S   L   I | 193 |
| cac gcg cgc aga acg tac cgg gag ctg cgg ctg ctc aag cac ctg aag<br> H   A   R   R   T   Y   R   E   L   R   L   L   K   H   L   K | 241 |
| cac gag aac gtc atc ggg ctt ctg gac gtc ttc acg ccg gcc acg tcc<br> H   E   N   V   I   G   L   L   D   V   F   T   P   A   T   S | 289 |
| atc gag gac ttc agc gaa gtg tac ttg gtg acc acc ctg atg ggc gcc<br> I   E   D   F   S   E   V   Y   L   V   T   T   L   M   G   A | 337 |
| gac ctg aac aac atc gtc aag tgc cag gcg ctg agc gac gag cac gtt<br> D   L   N   N   I   V   K   C   Q   A   L   S   D   E   H   V | 385 |
| caa ttc ctg gtt tac cag ctg ctg cgc ggg ctg aag tac atc cac tcg<br> Q   F   L   V   Y   Q   L   L   R   G   L   K   Y   I   H   S | 433 |
| gcc ggg atc atc cac cgg gac ctg aag ccc agc aac gtg gct gtg aac<br> A   G   I   I   H   R   D   L   K   P   S   N   V   A   V   N | 481 |
| gag gac tgt gag ctc agg atc ctg gat ttc ggg ctg gcg cgc cag gcg<br> E   D   C   E   L   R   I   L   D   F   G   L   A   R   Q   A | 529 |
| gac gag gag atg acc ggc tat gtg gcc acg cgc tgg tac cgg gca cct<br> D   E   E   M   T   G   Y   V   A   T   R   W   Y   R   A   P | 577 |
| gag atc atg ctc aac tgg atg cat tac aac caa aca gtg gat atc tgg<br> E   I   M   L   N   W   M   H   Y   N   Q   T   V   D   I   W | 625 |
| tcc gtg ggc tgc atc atg gct gag ctg ctc cag ggc aag gcc ctc ttc<br> S   V   G   C   I   M   A   E   L   L   Q   G   K   A   L   F | 673 |
| ccg gga agc gac tac att gac cag ctg aag cgc atc atg gaa gtg gtg<br> P   G   S   D   Y   I   D   Q   L   K   R   I   M   E   V   V | 721 |
| ggc aca ccc agc cct gag gtt ctg gca aaa atc tcc tcg gaa cac gcc<br> G   T   P   S   P   E   V   L   A   K   I   S   S   E   H   A | 769 |
| cgg aca tat atc cag tcc ctg ccc ccc atg ccc cag aag gac ctg agc<br> R   T   Y   I   Q   S   L   P   P   M   P   Q   K   D   L   S | 817 |

*Fig. 5A*

| | | | | | | | | | | | | | | | |
|---|---|---|---|---|---|---|---|---|---|---|---|---|---|---|---|
| agc | atc | ttc | cgt | gga | gcc | aac | ccc | ctg | gcc | ata | gac | ctc | ctt | gga | agg | 865
| S | I | F | R | G | A | N | P | L | A | I | D | L | L | G | R |

| atg | ctg | gtg | ctg | gac | agt | gac | cag | agg | gtc | agt | gca | gct | gag | gca | ctg | 913
| M | L | V | L | D | S | D | Q | R | V | S | A | A | E | A | L |

| gcc | cac | gcc | tac | ttc | agc | cag | tac | cac | gac | ccc | gag | gat | gag | cca | gag | 961
| A | H | A | Y | F | S | Q | Y | H | D | P | E | D | E | P | E |

| gcc | gag | cca | tat | gat | gag | ggc | gtt | gag | gcc | aag | gag | cgc | acg | ctg | gag | 1009
| A | E | P | Y | D | E | G | V | E | A | K | E | R | T | L | E |

| gag | tgg | aag | gag | ctc | act | tac | cag | gaa | gtc | ctc | agc | ttc | aag | ccc | cca | 1057
| E | W | K | E | L | T | Y | Q | E | V | L | S | F | K | P | P |

| gag | cca | ccg | aag | cca | cct | ggc | agc | ctg | gag | att | gag | cag | tgaggtgctg | | | 1106
| E | P | P | K | P | P | G | S | L | E | I | E | Q | | | | cccagcagcc cctgagagcc tgtggagggg cttgggcctg caccctttcca cagctggcct    1166 ggtttcctcg agaggcacct cccacactcc tatggtcaca gacttctggc ctaggacccc    1226 tcgccttcag gagaatctac acgcatgatg gagctgatcc agtaacctcg gagacgggac    1286 cctgcccaga gccgagttgg gggtgtggct ctccctgga aagggggtga cctcttgcct    1346 cgaggggccc agggaagcct gggtgtcaag tgcctgcacc agggggtgcac aataaagggg    1406 gttctctcta aaaaaaaaaa aaaaaaaaaa aaaaaaaaaa aaagcggccg ctgaattcta    1466 cctgcccggg cggccgctcg agccctatag tgagta    1502

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1502 base pairs
      (B) TYPE: nucleic acid
      (C) STRANDEDNESS: single
      (D) TOPOLOGY: linear (xi) SEQUENCE DESCRIPTION: SEQ ID NO: 1:

```
GGACATGTCG  GGCCCTCGCG  CCGGCTTCTA  CCGGCAGGAG  CTGAACAAGA  CCGTGTGGGA      60

GGTGCCCCAC  CCCCTCCAGG  GGCTGCGCCC  GGTCGGCTCC  GGCGCCTACG  GCTCCGTCTG     120

TTCGGCCTAC  GACGCCCGGC  TGCGCCAGAA  GGTGGCGGTG  AAGAAGCTGT  CGCGCCCCTT     180

CCAGTCGCTG  ATCCACGCGC  GCAGAACGTA  CCGGGAGCTG  CGGCTGCTCA  AGCACCTGAA     240

GCACGAGAAC  GTCATCGGGC  TTCTGGACGT  CTTCACGCCG  GCCACGTCCA  TCGAGGACTT     300
```

-continued

```
CAGCGAAGTG TACTTGGTGA CCACCCTGAT GGGCGCCGAC CTGAACAACA TCGTCAAGTG    360

CCAGGCGCTG AGCGACGAGC ACGTTCAATT CCTGGTTTAC CAGCTGCTGC GCGGGCTGAA    420

GTACATCCAC TCGGCCGGGA TCATCCACCG GGACCTGAAG CCCAGCAACG TGGCTGTGAA    480

CGAGGACTGT GAGCTCAGGA TCCTGGATTT CGGGCTGGCG CGCCAGGCGG ACGAGGAGAT    540

GACCGGCTAT GTGGCCACGC GCTGGTACCG GGCACCTGAG ATCATGCTCA ACTGGATGCA    600

TTACAACCAA ACAGTGGATA TCTGGTCCGT GGGCTGCATC ATGGCTGAGC TGCTCCAGGG    660

CAAGGCCCTC TTCCCGGGAA GCGACTACAT TGACCAGCTG AAGCGCATCA TGGAAGTGGT    720

GGGCACACCC AGCCCTGAGG TTCTGGCAAA AATCTCCTCG GAACACGCCC GGACATATAT    780

CCAGTCCCTG CCCCCCATGC CCCAGAAGGA CCTGAGCAGC ATCTTCCGTG GAGCCAACCC    840

CCTGGCCATA GACCTCCTTG AAGGATGCT GGTGCTGGAC AGTGACCAGA GGGTCAGTGC    900
```
(approximate — see image)

```
AGCTGAGGCA CTGGCCCACG CCTACTTCAG CCAGTACCAC GACCCCGAGG ATGAGCCAGA    960

GGCCGAGCCA TATGATGAGG GCGTTGAGGC CAAGGAGCGC ACGCTGGAGG AGTGGAAGGA   1020

GCTCACTTAC CAGGAAGTCC TCAGCTTCAA GCCCCCAGAG CCACCGAAGC CACCTGGCAG   1080

CCTGGAGATT GAGCAGTGAG GTGCTGCCCA GCAGCCCCTG AGAGCCTGTG GAGGGCTTG    1140

GGCCTGCACC CTTCCACAGC TGGCCTGGTT TCCTCGAGAG GCACCTCCCA CACTCCTATG   1200

GTCACAGACT TCTGGCCTAG GACCCCTCGC CTTCAGGAGA ATCTACACGC ATGATGGAGC   1260

TGATCCAGTA ACCTCGGAGA CGGGACCCTG CCCAGAGCCG AGTTGGGGGT GTGGCTCTCC   1320

CCTGGAAAGG GGGTGACCTC TTGCCTCGAG GGGCCCAGGG AAGCCTGGGT GTCAAGTGCC   1380

TGCACCAGG GTGCACAATA AAGGGGGTTC TCTCTAAAAA AAAAAAAAAA AAAAAAAAA     1440

AAAAAAAAAG CGGCCGCTGA ATTCTACCTG CCCGGGCGGC CGCTCGAGCC CTATAGTGAG   1500

TA                                                                1502
```

(2) INFORMATION FOR SEQ ID NO: 2:

(i) SEQUENCE CHARACTERISTICS:
        (A) LENGTH: 364 amino acids
        (B) TYPE: amino acid
        (C) STRANDEDNESS: single
        (D) TOPOLOGY: linear (xi) SEQUENCE DESCRIPTION: SEQ ID NO: 2:

```
Met Ser Gly Pro Arg Ala Gly Phe Tyr Arg Gln Glu Leu Asn Lys Thr
 1               5                  10                  15

Val Trp Glu Val Pro Gln Arg Leu Gln Gly Leu Arg Pro Val Gly Ser
            20                  25                  30

Gly Ala Tyr Gly Ser Val Cys Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Leu
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
        115                 120                 125

Phe Leu Val Tyr Gln Leu Leu Arg Gly Leu Lys Tyr Ile His Ser Ala
```

-continued

```
                130                 135                 140
Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                165                 170                 175

Glu Glu Met Thr Gly Tyr Val Ala Thr Arg Trp Tyr Arg Ala Pro Glu
                180                 185                 190

Ile Met Leu Asn Trp Met His Tyr Asn Gln Thr Val Asp Ile Trp Ser
                195                 200                 205

Val Gly Cys Ile Met Ala Glu Leu Leu Gln Gly Lys Ala Leu Phe Pro
                210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
                260                 265                 270

Ile Phe Arg Gly Ala Asn Pro Leu Ala Ile Asp Leu Leu Gly Arg Met
                275                 280                 285

Leu Val Leu Asp Ser Asp Gln Arg Val Ser Ala Ala Glu Ala Leu Ala
                290                 295                 300

His Ala Tyr Phe Ser Gln Tyr His Asp Pro Glu Asp Glu Pro Glu Ala
305                 310                 315                 320

Glu Pro Tyr Asp Glu Gly Val Glu Ala Lys Glu Arg Thr Leu Glu Glu
                325                 330                 335

Trp Lys Glu Leu Thr Tyr Gln Glu Val Leu Ser Phe Lys Pro Pro Glu
                340                 345                 350

Pro Pro Lys Pro Pro Gly Ser Leu Glu Ile Glu Gln
                355                 360
```

(2) INFORMATION FOR SEQ ID NO: 3:

(i) SEQUENCE CHARACTERISTICS:
        (A) LENGTH: 102 amino acids
        (B) TYPE: amino acid
        (C) STRANDEDNESS: single
        (D) TOPOLOGY: linear (xi) SEQUENCE DESCRIPTION: SEQ ID NO: 3:

```
Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
                20                  25                  30

Gly Ala Tyr Gly Ser Val Cys Ser Ala Tyr Asp Ala Arg Leu Arg Gln
                35                  40                  45

Lys Val Ala Val Lys Lys Leu Ser Arg Pro Phe Gln Ser Leu Ile His
50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val
                100
```

(2) INFORMATION FOR SEQ ID NO: 4:

-continued

```
    (i) SEQUENCE CHARACTERISTICS:
        (A) LENGTH: 155 amino acids
        (B) TYPE: amino acid
        (C) STRANDEDNESS: single
        (D) TOPOLOGY: linear (xi) SEQUENCE DESCRIPTION: SEQ ID NO: 4:

Met Ser Gly Pro Arg Ala Gly Phe Tyr Arg Gln Glu Leu Asn Lys Thr
1               5                  10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
            35                  40                  45

Lys Val Ala Val Lys Lys Leu Ser Arg Pro Phe Gln Ser Leu Ile His
        50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
            115                 120                 125

Phe Leu Val Tyr Gln Leu Leu Arg Gly Leu Lys Tyr Ile His Ser Ala
        130                 135                 140

Gly Ile Ile His Arg Val Gly Ala Thr Ala Gly
145                 150                 155
```

MITOGEN-ACTIVATED PROTEIN KINASE P38-2 AND METHODS OF USE THEREFOR

This is a continuation of application Ser. No. 09/295,029, filed Apr. 20, 1999, now U.S. Pat. No. 6,444,455, Jun. 13,2000, which is a divisional of application Ser. No. 08/651,940, filed May 20, 1996, now U.S. Pat. No. 5,948, 885, May 20, 1996 each of which are incorporated herein in their entireties.

TECHNICAL FIELD

The present invention relates generally to compositions and methods useful for the study of mitogen-activated protein kinase cascades and for treating diseases associated with such pathways. The invention is more particularly related to the mitogen-activated protein kinase p38-2, and variants thereof that stimulate phosphorylation and activation of substrates, such as ATF2. The present invention is also related to the use of such polypeptides to identify antibodies and other agents that inhibit or activate signal transduction via the p38-2 kinase cascade.

BACKGROUND OF THE INVENTION

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif with the sequence Thr-X-Tyr by mitogen-activated protein kinase kinases (MAPKKs). In higher eukaryotes, the physiological role of MAPK signaling has been correlated with cellular events such as proliferation, oncogenesis, development and differentiation. Accordingly, the ability to regulate signal transduction via these pathways could lead to the development of treatments and preventive therapies for human diseases associated with MAPK signaling, such as inflammatory diseases, autoimmune diseases and cancer.

In mammalian cells, three parallel MAPK pathways have been described. The best characterized pathway leads to the activation of the extracellular-signal-regulated kinase (ERK). Less well understood are the signal transduction pathways leading to the activation of the cJun N-terminal kinase (JNK) and the p38 MAPK (for reviews, see Davis, Trends Biochem. Sci. 19:470–473 (1994); Cano and Mahadevan, Trends Biochem. Sci. 20:117–122(1995)). The identification and characterization of members of these cascades is critical for understanding the signal transduction pathways involved and for developing methods for activating or inactivating MAPKs in vivo.

Three MAPKKs capable of activating p38 in vitro have been identified. MKK3 appears to be specific for p38 (i.e., does not activate JNK or ERK), while MKK4 activates both p38 and JNK (see Derijard et al., Science 267:682–685, 1995). The third MAPKK, MEK6, appears to be a stronger and more specific in vivo stimulator of p38 phosphorylation (see U.S. patent application Ser. No. 08/576,240). These proteins appear to have utility in therapeutic methods for treating conditions associated with the p38 signal transduction pathway. However, in order to precisely tailor such therapeutic methods, and to gain an understanding of the pathways involved, it would be advantageous to identify and characterize other proteins that participate in this cascade and related MAP kinase cascades.

Accordingly, there is a need in the art for improved methods for modulating the activity of proteins involved in the MAP kinase cascades, and for treating diseases associated with such cascades. The present invention fulfills these needs and further provides other related advantages.

SUMMARY OF THE INVENTION

Briefly stated, the present invention provides compositions and methods employing the mitogen-activated protein kinase (MAPK) p38-2, or a variant thereof. In one aspect, the present invention provides polypeptides comprising the amino acid sequence provided in SEQ ID NO:2 or a variant thereof that differs only in conservative substitutions and/or modifications at no more than 25% of the amino acid residues. Such variants include constitutively active polypeptides. In a related aspect, polypeptides comprising the amino acid sequence provided in SEQ ID NO:2 modified at no more than 25% of the amino acid residues, such that the polypeptides are rendered constitutively inactive, are provided.

In other aspects, isolated DNA molecules encoding polypeptides as described above, as well as recombinant expression vectors comprising such DNA molecules and host cells transformed or tansfected with such expression vectors, are provided.

In another aspect, the present invention provides methods for phosphorylating a substrate of p38-2, comprising contacting a polypeptide as described above with a substrate of p38-2, thereby phosphorylating the substrate of p38-2. In a related aspect, methods are provided for activating a substrate of p38-2 in a patient, comprising administering to a patient a polypeptide as described above in combination with a pharmaceutically acceptable carrier, thereby activating a substrate of p38-2.

In further aspects, the present invention provides methods for screening for an agent that modulates signal transduction via the p38-2 cascade. In one embodiment the method comprises: (a) contacting a candidate agent with a polypeptide as described above, wherein the step of contacting is carried out under conditions and for a time sufficient to allow the candidate agent and the polypeptide to interact; and (b) subsequently measuring the ability of the candidate agent to modulate p38-2 activity, and thereby evaluating the ability of the candidate agent to modulate signal transduction via the p38 cascade. In another embodiment, the method comprises: (a) contacting a candidate agent with a polynucleotide encoding a polypeptide as described above, wherein the step of contacting is carried out under conditions and for a time sufficient to allow generation of the polypeptide and interaction between the polypeptide and the candidate agent; and (b) subsequently measuring the ability of the candidate agent to modulate p38-2 activity, and thereby evaluating the ability of the candidate agent to modulate signal transduction via the p38-2 cascade.

In yet another aspect, the present invention provides antibodies that bind to a polypeptide as described above.

In further aspects, methods are provided for treating a disorder associated with the p38-2 cascade, comprising administering to a patient a therapeutically effective amount of an agent that modulates signal transduction via the p38-2 cascade. In related aspects, methods are provided for treating a patient afflicted with a disease associated with the p38-2 cascade, comprising administering to a patient an agent that inhibits p38-2 kinase activity or that inhibits phosphorylation of p38-2.

In still further aspects, the present invention provides methods and kits for detecting mitogen activated protein kinase kinase activity in a sample. The methods comprise evaluating the ability of the sample to phosphorylate a polypeptide as described above, thereby detecting mitogen activated protein kinase kinase activity in the sample. Kits comprise p38-2 in combination with a suitable buffer.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 presents the primary amino acid sequence of p38-2 (SEQ ID NO:2), and splice variants thereof, (SEQ ID NO:3 and SEQ ID NO:4), using standard one-letter codes.

FIG. 5 presents the nucleotide (SEQ ID NO:1) and amino acid sequence of p38-2.

DETAILED DESCRIPTION OF THE INVENTION

Figure 2A:
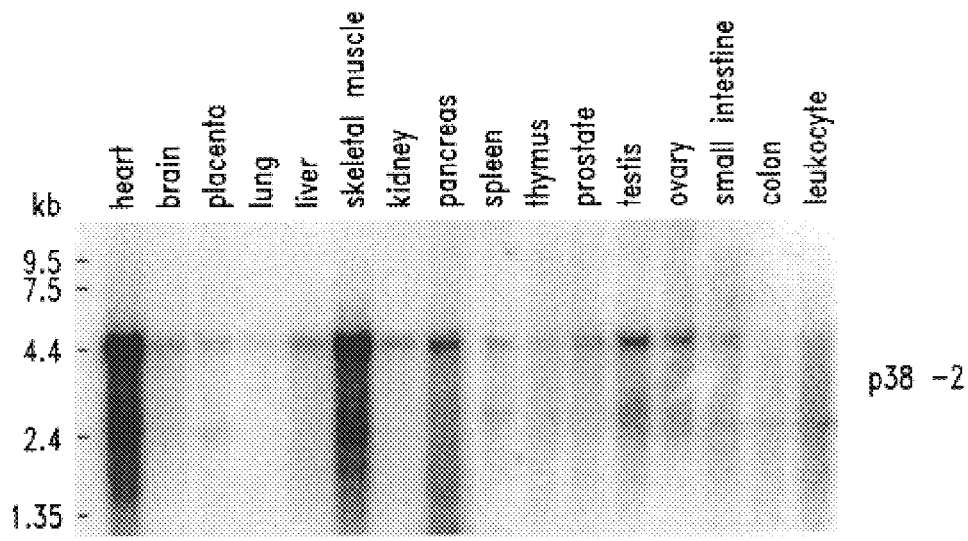
FIGS. 2A and 2B are autoradiograms that depict Northern blot analyses of the expression of human p38-2 (FIG. 2A) and p38 (FIG. 2B) mRNA in selected human tissues. The position of RNA size markers in kb is shown on the left.

As noted above, the present invention is generally directed to compositions and methods for modulating (i.e., stimulating or inhibiting) signal transduction via MAP kinase cascades. In particular, the present invention is directed to compositions comprising the MAP kinase p38-2 or a polypeptide variant thereof, and to the use of such compositions for activating substrates of p38-2 and for identifying modulators of p38-2 activity. As used herein, the term "p38-2 polypeptide" encompasses the native p38-2 sequence, as well as variants thereof. The present invention also encompasses compositions and methods for modulating p38-2 activity. In general, compositions that inhibit p38-2 activity may inhibit p38-2 phosphorylation, or may inhibit the ability of p38-2 to phosphorylate a substrate. As used herein, the term "p38-2 cascade" refers to any signal transduction pathway that involves p38-2, and such a cascade may include any compound that modulates p38-2 activity or acts as a substrate for p38-2.

p38-2 polypeptide variants within the scope of the present invention may contain one or more conservative substitutions and/or modifications at no more than 25% of the amino acid residues in the native polypeptide, such that the ability of the variant to phosphorylate substrates (such as ATF2, MAPKAP kinase 2 and MAPKAP kinase 3) is not substantially diminished. Preferably, a variant contains substitutions and/or modifications at no more than 20% of the amino acid residues, and more preferably at no more than 10% of residues. Such substitutions, which are preferably conservative, may be made in noncritical and/or critical regions of the native protein. Variants may also, or alternatively, contain other modifications, including the deletion or addition of amino acids that have minimal influence on the activity of the polypeptide. In particular, variants may contain additional amino acid sequences at the amino and/or carboxy temini. Such sequences may be used, for example, to facilitate purification or detection of the polypeptide.

Substitutions and/or modifications may also be made at no more than 25% (preferably at no more than 20%, and more preferably at no more than 10%) of amino acid residues to render the polypeptide constitutively active or inactive. Constitutively active polypeptides display the ability to stimulate substrate phosphorylation in the absence of stimulation, as described below. Such variants may be identified using the representative assays for p38-2 kinase activity described herein. Constitutively inactive proteins are those which are unable to phosphorylate a substrate even when stimulated as described below. Proteins modified so as to be constitutively active or inactive may generally be used in replacement therapy for treatment of a variety of disorders, as discussed in more detail below.

DNA sequences encoding native p38-2 may be prepared by amplification from a suitable human cDNA library, using polymerase chain reaction (PCR) and methods well known to those of ordinary skill in the art. For example, an adapter-ligated cDNA library prepared from a cell line or tissue that expresses p38-2 (such as skeletal muscle or heart) may be screened using a 5' specific forward primer and an adapter-specific primer. The resulting 1.6 kb cDNA has the sequence provided in SEQ ID NO:1 and FIG. 5. The encoded p38-2 polypeptide, shown in SEQ ID NO:2 and FIG. 1, has a predicted size of 364 amino acids, with a molecular weight of about 42 kD as determined by calculation and SDS-polyacrylamide gel electrophoresis. p38-2 is 73% identical to its closest homolog p38 (see, e.g., Han et al., *Science* 265:808–811, 1994); Lee et al., *Nature* 372:739–746, 1994), and all kinase subdomains characteristic for MAP kinase family members are conserved. Two alternate splice variants of p38-2 have also been identified, with the sequences provided in FIG. 1, as well as SEQ ID NO:3 and SEQ ID NO:4.

Polypeptides of the present invention may be prepared by expression of recombinant DNA encoding the polypeptide in cultured host cells. Preferably, the host cells are bacteria, yeast, baculovirus-infected insect cells or mammalian cells. The recombinant DNA may be cloned into any expression vector suitable for use within the host cell, using techniques well known to those of ordinary skill in the art. An expression vector may, but need not, include DNA encoding an epitope, such that the recombinant protein contains the epitope at the N- or C-terminus. Epitopes such as glutathione-S transferase protein (GST), HA (hemagglutinin)-tag, FLAG and Histidine-tag may be added using techniques well known to those of ordinary skill in the art.

The DNA sequences expressed in this manner may encode p38-2, or may encode alternate splice variants, portions or other variants of p38-2, as well as constitutively inactive polypeptides. DNA molecules encoding variants of p38-2 may generally be prepared using standard mutagenesis techniques, such as oligonucleotide directed site-specific mutagenesis, and sections of the DNA sequence may be removed to permit preparation of truncated polypeptides. As noted above, up to 25% of the amino acid residues may contain substitutions or other modifications. For variants of p38-2, any such changes should not diminish the ability of the variant to stimulate phosphorylation of substrates such as ATF2 (see, e.g., Gupta et al., *Science* 267:389–393, 1995), MAPKAP kinase 2 (see, e.g., Rouse et al., *Cell* 78:1027–1037, 1994 Ben Levy et al., *EMBO J*: 14:5920–6930, 1995) or MAPKAP kinase 3 (see e.g., McLaughlin et al., *J Biol. Chem.* 271:8488–8492, 1996). In general, modifications may be more readily made in non-critical regions, which are regions of the native sequence that do not substantially change the properties of p38-2. Non-critical regions may be identified by modifying the p38-2 sequence in a particular region and assaying the ability of the resulting variant in a kinase assay, using a suitable substrate, as described herein.

Modifications may also be made in critical regions of p38-2, provided that the resulting variant substantially retains the ability to stimulate substrate phosphorylation. The effect of any modification on the ability of the variant to stimulate substrate phosphorylation may generally be evaluated using any assay for p38-2 kinase activity, such as the representative assays described herein.

Expressed polypeptides of this invention are generally isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography. p38-2 polypeptides for use in the methods of the present invention may be native, purified or recombinant.

In one aspect of the present invention, p38-2 polypeptides may be used to identify modulating agents, which may be antibodies or drugs, that inhibit or stimulate signal transduction via the p38-2 cascade. Modulation includes the suppression of expression of p38-2 when it is over expressed, or the augmentation of p38-2 expression when it is under expressed. Modulation may also include suppression of phosphorylation of p38-2 or the stimulation or inhibition of the ability of activated (i.e., phosphorylated) p38-2 to phosphorylate a substrate. For example, a modulating agent may modulate the kinase activity of one or more MAPKKs, such as MEK6, thereby stimulating or inhibiting p38-2 activation. Known activators of MAPKKs include, but are not limited to, stress-inducing signals (e.g., V, osmotic shock, DNA-damaging agents), anisomycin, LPS, and cytokines. Similarly, compositions that inhibit p38-2 activity by inhibiting p38-2 phosphorylation may include one or more agents that inhibit or block MAPKK activity, such as an antibody that neutralizes a MAPKK, a competing peptide that represents the substrate binding domain of a MAPKK or the dual phosphorylation motif of p38-2, an antisense polynucleotide or ribozyme that interferes with transcription and/or translation of a MAPKK, a molecule that inactivates a MAPKK by binding to the kinase, a molecule that binds to p38-2 and prevents phosphorylation by a MAPKK or a molecule that prevents transfer of phosphate groups from the kinase to the substrate.

In general, modulating agents may be identified by combining a test compound with a p38-2 polypeptide (which may be activated or constitutively active), or a polynucleotide encoding such a polypeptide, in vitro or in vivo, and evaluating the effect of the test compound on the p38-2 kinase activity using, for example, a representative assay described herein. An increase or decrease in kinase activity can be measured by adding a radioactive compound, such as $^{32}$P-ATP, to the mixture of components, and observing radioactive incorporation into a suitable substrate for p38-2, to determine whether the compound inhibits or stimulates kinase activity. Briefly, a candidate agent may be included in a mixture of active p38-2 polypeptide and substrate (such as ATF2), with or without pre-incubation with one or more components of the mixture. Activation of p38-2 may be achieved by any of a variety of means. Typically, activation involves the addition of a MAP kinase kinase, which may in turn be activated via stimulation as described above. In general, a suitable amount of antibody or other agent for use in such an assay ranges from about 0.1 $\mu$M to about 10 $\mu$M. The effect of the agent on p38-2 kinase activity may then be evaluated by quantitating the incorporation of [$^{32}$P] phosphate into ATF2, and comparing the level of incorporation with that achieved using activated p38-2 without the addition of a candidate agent. Alternatively, a polynucleotide encoding the kinase may be inserted into an expression vector and the effect of a composition on transcription of the kinase measured, for example, by Northern blot analysis.

In another aspect of the present invention, a p38-2 polypeptide (which may be constitutively active) may be used for phosphorylating and activating a substrate of p38-2. In one embodiment, a substrate may be phosphorylated in vitro by incubating a p38-2 polypeptide with a substrate and ATP in a suitable buffer (described in more detail below) for 30 minutes at 30° C. Any compound that can be phosphorylated by p38-2, such as ATF2, MAPKAP kinase 2 and MAPKAP kinase 3 may be used as a substrate. In general, the amounts of the reaction components may range from about 0.1 $\mu$g to about 10 $\mu$g of p38-2 polypeptide, from about 0.1 $\mu$g to about 10 $\mu$g of substrate, and from about 10 nM to about 500 nM of ATP. Phosphorylated substrate may then be purified by binding to GSH-sepharose and washing. The extent of substrate phosphorylation may generally be monitored by adding [$\gamma$-$^{32}$P]ATP to a test aliquot, and evaluating the level of substrate phosphorylation as described below.

One or more p38-2 polypeptides, modulating agents as described above and/or polynucleotides encoding such polypeptides and/or modulating agents may also be used to modulate p38-2 activity in a patient. As used herein, a "patient" may be any mammal, including a human, and may be afflicted with a disease associated with the p38-2 cascade or may be free of detectable disease. Accordingly, the treatment may be of an existing disease or may be prophylactic. Diseases associated with the p38-2 cascade include any disorder which is etiologically linked to MAP kinase activity, including cardiovascular disease, immune-related diseases (e.g., inflammatory diseases, autoimmune diseases, malignant cytokine production or endotoxic shock), cell growth-related diseases (e.g., cancer, metabolic diseases, abnormal cell growth and proliferation or cell cycle abnormalities) and cell regeneration-related diseases (e.g., cancer, degenerative diseases, trauma, environmental stress by heat, UV or chemicals or abnormalities in development and differentiation). In particular, the high expression of p38-2 in heart tissue suggests an important role for p38-2 in cardiovascular diseases. Immunological-related cell proliferative diseases appropriate for treatment with p38-2 polypeptides include osteoarthritis, ischemia, reperfusion injury, trauma, certain cancers and viral disorders, and autoimmune diseases such as rheumatoid arthritis, multiple sclerosis, psoriasis, inflammatory bowel disease, and other acute phase responses.

Treatment may include administration of a p38-2 polypeptide and/or a compound which modulates p38-2 activity. For administration to a patient, one or more polypeptides (and/or modulating agents) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a p38-2 polypeptide, and/or modulating agent, such that the polypeptide and/or modulating agent is generated in situ, in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–1749 (1993).

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA 12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for p38-2 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (ie., an artificial membrane vesicle). It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well doses, will vary from patient to patient. In general, the pharmaceutical compositions may be administered intravenously, intraperitoneally, intramuscularly, subcutaneously, inactivity or transdermally. Between 1 and 6 doses may be administered daily. A suitable dose is an amount of polypeptide or polynucleotide that is sufficient to show improvement in the symptoms of a patient afflicted with a disease associated with the p38-2 cascade.

Such improvement may be detected based on a determination of relevant cytokine levels (e.g., IL-1, IL-6 and/or IL-8), by monitoring inflammatory responses (e.g, edema, transplant rejection, hypersensitivity) or through an improvement in clinical symptoms associated with the disease. In general, the amount of polypeptide present in a dose, or produced in situ by DNA present in a dose, ranges from about 1 $\mu$g to about 250 $\mu$g per kg of host, typically from about 1 $\mu$g to about 60 $\mu$g. Suitable dose sizes will vary with the size of the patient, but will typically range from about 10 mL to about 500 mL for 10–60 kg animal.

The present invention also provides methods for detecting the level of mitogen activated protein kinase kinase (such as MEK6) activity in a sample. The level of MAPKK activity may generally be determined by evaluating the ability of the sample to phosphorylate a p38-2 polypeptide, thereby rendering the p38-2 polypeptide active (i.e., capable of phosphorylating in vivo substrates such as ATF2). In one embodiment, a kinase assay may be performed substantially as described in Derijard et al., *Cell* 76:1025–1037, 1994 and Lin et al., *Science* 268:286–290, 1995, with minor modifications. Briefly, a sample may be incubated with p38-2 and [γ-$^{32}$P]ATP in a suitable buffer (such as 20 mM HEPES (pH 7.6), 5 mM MnCl$_2$, 10 mM MgCl$_2$, 1 mM dithiothreitol) for 30 minutes at 30° C. In general, approximately 1 μg recombinant p38-2, with 50 nM [γ-$^{32}$P]ATP, is sufficient. Proteins may then be separated by SDS-PAGE on 10% gels and subjected to autoradiography. Incorporation of [$^{32}$P] phosphate into p38-2 may be quantitated using techniques well known to those of ordinary skill in the art, such as with a phosphorimager.

To determine whether p38-2 phosphorylation results in activation, a coupled in vitro kinase assay may be performed using a substrate for p38-2, such as ATF2, with or without an epitope tag. ATF2 for use in such an assay may be prepared as described in Gupta et al., *Science* 267:389–393, 1995. Briefly, following phosphorylation of p38-2 as described above, isolation of the protein by binding to GSH-sepharose and washing with 20 mM HEPES (pH 7.6), 20 mM MgCl$_2$, the p38-2 (0.1–10 μg) may be incubated with ATF2 (0.1–10 μg) and [γ-$^{32}$P]ATP (10–500 nM) in a buffer containing 20 mM HEPES (pH 7.6), 20 mM MgCl$_2$. It should be noted that alternative buffers may be used and that buffer composition can vary without significant effects on kinase activity. Reactions may be separated by SDS-PAGE, visualized by autoradiography and quantitated using any of a variety of known techniques. Activated p38-2 will be capable of phosphorylating ATF2 at a level of at least 5% above background using this assay.

To evaluate the effect of an antibody or other candidate modulating agent on the level of signal transduction via the p38-2 cascade, a kinase assay may be performed as described above, except that a MAPKK, such as MEK6 (rather than a sample) is generally employed and the candidate modulating agent is added to the incubation mire. The candidate agent may be preincubated with MAPKK before addition of ATP and p38-2 polypeptide. Alternatively, the p38-2 may be preincubated with the candidate agent before the addition of MAPKK. Further variations include adding the candidate agent to a mixture of MAPKK and ATP before the addition of p38-2, or to a mixture of p38-2 and ATP before the addition of MAPKK, respectively. To identify modulators that inhibit the kinase activity of activated p38-2, a constitutively active variant of p38-2 may be employed. All these assays can further be modified by removing the candidate agent after the initial preincubation step. In general, a suitable amount of antibody or other candidate agent for use in such an assay ranges from about 0.1 μM to about 10 μM. The effect of the agent on phosphorylation of p38-2 may then be evaluated by quantitating the incorporation of [$^{32}$P]phosphate into p38, as described above, and comparing the level of incorporation with that achieved using MAPKK without the addition of the candidate agent.

p38-2 activity may also be measured in whole cells transfected with a reporter gene whose expression is dependent upon the activation of an appropriate substrate, such as ATF2. For example, appropriate cells (i.e., cells that express p38-2) may be transfected with an ATF2-dependent promoter linked to a reporter gene such as luciferase. In such a system, expression of the luciferase gene (which may be readily detected using methods well known to those of ordinary skill in the art) depends upon activation of ATF2 by p38-2, which may be achieved by the stimulation of MAPKK with an activator or by cotransfection with an expression vector that produces a constitutively active variant of MAPKK, such as MEK6. Candidate modulating agents may be added to the system, as described above, to evaluate their effect on the p38-2 cascade.

Alternatively, a whole cell system may employ only the trasactivation domain of ATF2 fused to a suitable DNA binding domain, such as GHF-1 or GAL4. The reporter system may then comprise the GH-luciferase or GAL4-luciferase plasmid. Candidate modulating agents may then be added to the system to evaluate their effect on ATF2-specific gene activation.

The present invention also provides methods for detecting the level of p38-2 polypeptide in a sample. The level of p38-2, or nucleic acid encoding p38-2, may generally be determined using a reagent that binds to p38-2, or to DNA or RNA encoding p38-2. To detect nucleic acid encoding p38-2, standard hybridization and/or PCR techniques may be employed using a nucleic acid probe or a PCR primer. Suitable probes and primers may be designed by those of ordinary skill in the art based on the p38-2 cDNA sequence provided in SEQ ID NO:1. To detect p38-2 protein, the reagent is typically an antibody, which may be prepared as described below. There are a variety of assay formats known to those of ordinary skill in the art for using an antibody to detect a polypeptide in a sample. See, e.g., Harlow and Lane, *Antibodies: A Laboratory Manual*, Cold Spring Harbor Laboratory, 1988. For example, the antibody may be immobilized on a solid support such that it can bind to and remove the polypeptide from the sample. The bound polypeptide may then be detected using a second antibody that binds to the antibody/peptide complex and contains a detectable reporter group. Alternatively, a competitive assay may be utilized, in which polypeptide that binds to the immobilized antibody is labeled with a reporter group and allowed to bind to the immobilized antibody after incubation of the antibody with the sample. The extent to which components of the sample inhibit the binding of the labeled polypeptide to the antibody is indicative of the level of polypeptide within the sample. Suitable reporter groups for use in these methods include, but are not limited to, enzymes (e.g., horseradish peroxidase), substrates, cofactors, inhibitors, dyes. radionuclides, luminescent groups, fluorescent groups and biotin.

Antibodies encompassed by the present invention may be polyclonal or monoclonal, and may be specific for p38-2 and/or one or more variants thereof. Preferred antibodies are those antibodies that inhibit or block p38-2 activity in vivo and within an in vitro assay, as described above. As noted above, antibodies and other agents having a desired effect on p38-2 activity, may be administered to a patient (either prophylactically or for treatment of an existing disease) to modulate the activation of p38-2 in vivo.

Antibodies may be prepared by any of a variety of techniques known to those of ordinary skill in the art (see, e.g., Harlow and Lane, *Antibodies: A Laboratory Manual*, Cold Spring Harbor Laboratory, 1988). In one such technique, an immunogen comprising the polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for p38-2 or a variant thereof may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (ie., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thyraidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

In a related aspect of the present invention, kits for detecting p38-2 and p38-2 kinase activity, as well as MAPKK kinase activity, are provided. Such kits may be designed for detecting the level of p38-2 or nucleic acid encoding p38-2, or may detect kinase activity of p38-2 or MAPKK in a direct kinase assay or a coupled kinase assay, in which both the level of phosphorylation and the kinase activity of p38-2 may be determined. MAPKK or p38-2 kinase activity may be detected in any of a variety of samples, such as eukaryotic cells, bacteria, viruses, extracts prepared from such organisms and fluids found within living organisms. In general, the kits of the present invention comprise one or more containers enclosing elements, such as reagents or buffers, to be used in the assay.

A kit for detecting the level of p38-2, or nucleic acid encoding p38-2, typically contains a reagent that binds to the p38-2 protein, DNA or RNA. To detect nucleic acid encoding p38-2, the reagent may be a nucleic acid probe or a PCR primer. To detect p38-2 protein, the reagent is typically an antibody. Such kits also contain a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

Kits for detecting p38-2 activity typically comprise a p38-2 substrate in combination with a suitable buffer. p38-2 activity may be specifically detected by performing an immunoprecipitation step with a p38-2-specific antibody prior to performing a kinase assay as described above. Alternatively, the substrate provided may be a substrate that is phosphorylated only by p38-2 (i.e., is not phosphorylated by p38). A kit for detecting MAPKK kinase activity based on measuring the phosphorylation of p38-2 generally comprises a p38-2 polypeptide in combination with a suitable buffer. A kit for detecting MAPKK kinase activity based on detecting p38-2 activity generally comprises a p38-2 polypeptide in combination with a suitable p38-2 substrate, such as ATF2. Optionally, a kit may additionally comprise a suitable buffer and/or material for purification of p38 after activation and before combination with ATF2. Other reagents for use in detecting phosphorylation of p38-2 and/or kinase activity may also be provided. Such kits may be employed in direct or coupled kinase assays, which may be performed as described above.

In yet another aspect, p38-2 or a variant thereof may be used to identify one or more native upstream kinases (i.e., kinases that phosphorylate and activate p38-2 in vivo). A p38-2 polypeptide may be used in a yeast two-hybrid system to identify proteins that interact with p38-2. Alternatively, an expression library may be sequenced for cDNAs that phosphorylate p38-2.

The following Examples are offered by way of illustration and not by way of limitation.

EXAMPLES

Example 1

Cloning and Sequencing cDNA Encoding p38-2

This Example illustrates the cloning of a cDNA molecule encoding the human MAPK p38-2.

The Expressed Sequence Tags (EST) subdivision of the National Center for Biotechnology Information (NCBI) Genbank databank was searched with the tblastn program and the human p38 amino acid sequence (Han et al., *Science* 265:808–811, 1994; Lee et al., *Nature* 372:739–746, 1994) as query using the BLAST e-mail server. The EST sequence R72598 from a breast cDNA library displayed the highest similarity score. A clone corresponding to the EST sequence R72598 was obtained from Research Genetics Inc., (Huntsville, Ala.), and the insert size was determined to be about 0.9 kb. Sequencing revealed that this clone encodes the 5' portion of a previously unknown gene and that the 3' end with the polyA tail was missing. The 3' portion was obtained from a skeletal muscle cDNA library by RACE PCR using a gene specific forward primer and an adapter-based reverse primer. The complete cDNA was obtained by fusion ligation of the 5' portion and the 3' portion using a common KpnI site into pBluescript (Stratagene, La Jolla, Calif.), and verified by miniprep analysis.

Full length clones with and without an intron were identified. The sequences were obtained using dye terminator cycle sequencing with an ABI 373 Automated Sequencer (Applied Biosystems, Inc., Foster City, Calif.), and the sequence of the full length clone without intron is shown in SEQ ID NO:1 and FIG. 5.

Example 2

In vivo Expression of p38-2

This Example illustrates the expression of p38-2, as compared to p38, in various human tissues.

Northern blots were performed using 2 $\mu$g of polyA$^+$RNA isolated from 16 different adult human tissues, fractionated by denaturing formaldehyde 1.2% agarose gel electrophoresis, and transferred onto a charge-modified nylon membrane (Clontech Laboratories, Palo Alto, Calif.). The blots were hybridized to a p38-2 probe (900 bp p38-2 fragment) or p38 probe (850 bp p38 fragment) using ExpressHyb (Clontech Laboratories, Palo Alto, Calif.) according to the manufacturer's instructions. Both probes were prepared by labeling the cDNA with [$\alpha$-$^{32}$P]dCTP (NEN, Boston, Mass.) by random priming (Stratagene, La Jolla, Calif.). For control purposes, the blots were also hybridized to a radiolabeled β-actin probe.

Figure 2B:
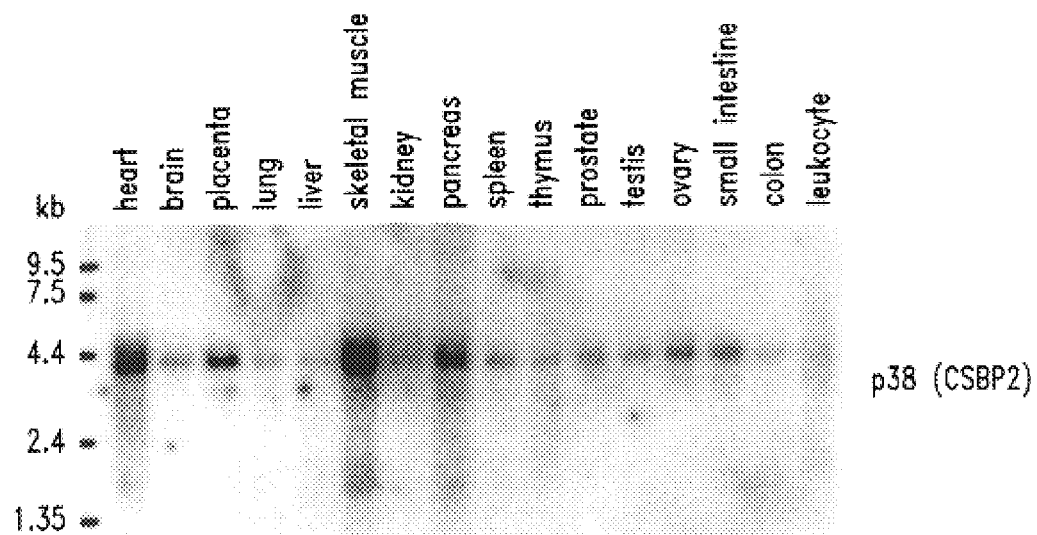

The results, shown in FIGS. 2A and 2B, demonstrate that p38-2 is widely expressed in many adult human tissues, with highest levels in heart and skeletal muscle (FIG. 2A). In contrast, p38 is predominantly expressed in skeletal muscle only (FIG. 2B). In addition, expression of p38-2 is higher than p38 in heart and testis, whereas expression of p38 is higher than p38-2 in placenta and small intestine. All 16 tissues analyzed expressed equal amounts of β-actin mRNA (not shown).

Example 3

Preparation of p38-2

This Example illustrates the in vitro translation of HA-tagged p38-2.

Figure 3:
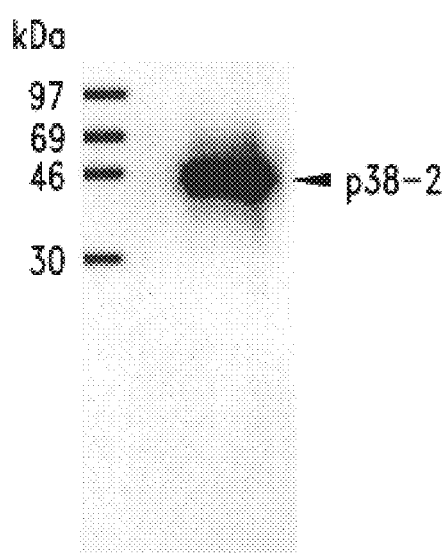
FIG. 3 is an autoradiogram that shows the size of in vitro translated HA-tagged p38-2, as determined by SDS-PAGE. The position of protein size markers in kDa is shown on the left.

HA tagged p38-2 was in vitro transcribed and translated using the Promega TNT Coupled Reticulocyte Lysate System (Promega, Madison, Wis.) in the presence of 35S-methionine using SP6 polymerase and the template DNA 3xHA-p38-2-SRα3). Radioactive, in vitro-translated proteins were separated by SDS-PAGE and visualized by autoradiography (FIG. 3).

These results demonstrate that the molecular weight of the epitope tagged p38-2 is approximately 42 kDa.

Example 4

Activation of p38-2 by Stress-inducing Agents

This Example illustrates the activation of p38-2 a variety of stimulators of the MAPK pathway.

An expression vector encoding epitope-tagged p38-2 (3xHA-p38-2-SRα3) was constructed by adding sequence encoding three copies of a 10 amino acid hemagglutinin (HA) epitope to the N-terminus of p38-2 and ligating the resulting cDNA into the expression vector SRα3. To investigate the pattern of regulation of p38-2, COS cells were transiently transfected with HA-p38-2-SRα3 (as described above) by the DEAE-Dextran method (Kawai and Nishizawa, Mol. Cell. Biol. 4:1172–1174, 1984). These cells were then treated with various stimulators of the MAPK pathway (i.e., treated for 45 minutes with UV (250 nm, 120 J/m2), anisomycin (50 ng/ml) or NaCl (200 μM) or cotransfected with 1000 ng of the empty expression vector Srα3, the expression vector for the constitutively active mutant MEK6(DD) or the MAPK TAK1ΔN).

Following treatment, cell lysates were prepared by solubilization in lysis buffer as described (Derijard et al., Cell 76:1025–1037, 1994), and protein concentration of lysates was determined by Bradford assay (Bradford, Ann. Biochem. 72:248–254, 1976). Cell lysates were used in an immune complex kinase assay with GST-ATF2 substrate, prepared as previously described (Gupta et al., Science 267:389–39, 1995). The assay was generally performed as described previously (Derijard et al., Cell 76:1025–1037, 1994; Lin et al., Science 268:286–290, 1995) with minor modifications. The concentration of [$\gamma$-$^{32}$P]ATP was 50 nM, and 30 μg cell lysate was immunoprecipitated for 2 hours with the anti-HA antibody 12CA5 (Boehringer-Mannheim Corp., Indianapolis, Ind.) and then incubated with 1 μg of recombinant substrate. Reactions were separated by SDS-PAGE, and the results are presented in FIG. 4.

Figure 4:
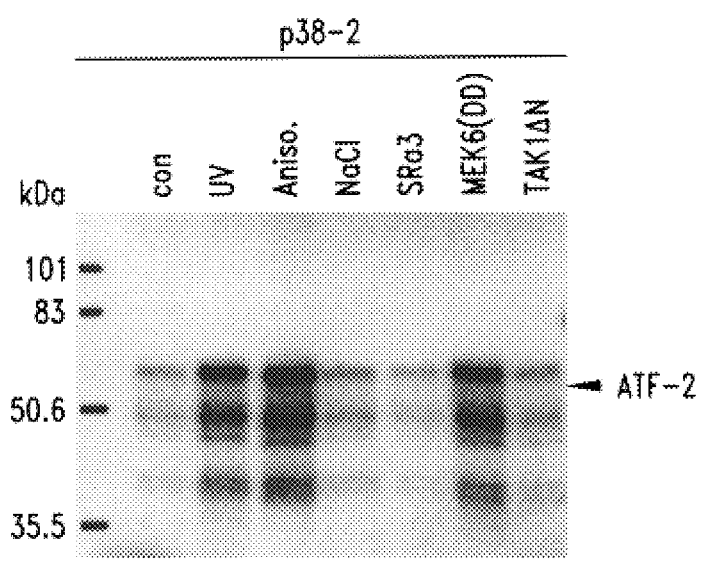
FIG. 4 is an autoradiogram presenting the relative levels of p38-2 kinase activity in COS cells transiently infected with epitope tagged p38-2 (lanes 1 to 7) and treated for 45 minutes with UV (250 nm, 120 J/m$^2$; lane 2), anisomycin (50 ng/ml; lane 3), or NaCl (200 $\mu$M; lane 4), or cotransfected with 1000 ng of the empty expression vector Sr$\alpha$3 (lane 5), the expression vector for the constitutively active mutant MEK6(DD) (lane 6) or the MAPK TAK1$\Delta$N (lane 7).

These experiments showed a strong induction of p38-2 by UV (254 nm; 120 J/m2 for 45 minutes), anisomycin (50 ng/ml for 45 minutes) and MEK6(DD), a constitutively active variant of MEK6 (FIG. 4). No increase in p38-2 activity was observed when the cells were treated with NaCl, expression vector alone or the MAP kinase TAK1ΔN (see Yamaguchi et al., Science 270:2008–2011, 1995). This clearly indicates that the inducible phosphorylation of ATF2 depends on a kinase cascade comprised of MEK6 and p38-2.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising a variant of the amino acid sequence provided in SEQ ID NO:2 that differs from SEQ ID NO:2 at no more than 20% of the amino acid residues of SEQ ID NO:2, wherein said polypeptide retains the ability to phosphorylate a substrate.

2. A kit for detecting mitogen activated protein kinase kinase activity in a sample, comprising a polypeptide of claim 1 in combination with a suitable buffer.

3. An isolated polypeptide consisting of the amino acid sequence of SEQ ID NO:3.

4. An isolated polypeptide consisting of the amino acid sequence of SEQ ID NO:4.

5. The isolated polypeptide of claim 1 wherein said polypeptide is constitutively active.

* * * * *